(12) United States Patent
Golan (10) Patent No.: US 9,895,216 B2
(45) Date of Patent: Feb. 20, 2018

(54) PERCUTANEOUS EMBOLI PROTECTION SLEEVE

(71) Applicant: Pi-Cardia Ltd., Rehovot (IL)

(72) Inventor: Erez Golan, Rehovot (IL)

(73) Assignee: PI-CARDIA LTD., Rehovot (IL)

( * ) Notice: Subject to any disclaimer, the term of this patent is extended or adjusted under 35 U.S.C. 154(b) by 285 days.

(21) Appl. No.: 14/390,836

(22) PCT Filed: Apr. 5, 2013

(86) PCT No.: PCT/US2013/035346
§ 371 (c)(1),
(2) Date: Oct. 6, 2014

(87) PCT Pub. No.: WO2013/152244
PCT Pub. Date: Oct. 10, 2013

(65) Prior Publication Data
US 2015/0032148 A1    Jan. 29, 2015

Related U.S. Application Data (60) Provisional application No. 61/621,005, filed on Apr. 6, 2012, provisional application No. 61/639,929, filed on Apr. 29, 2012.

(51) Int. Cl.
*A61M 29/00*   (2006.01)
*A61F 2/01*    (2006.01)
*A61B 17/00*   (2006.01)
*A61B 17/3207* (2006.01)
*A61B 17/22*   (2006.01)

(52) U.S. Cl.
CPC .......... *A61F 2/013* (2013.01); *A61B 17/3207* (2013.01); *A61B 2017/00783* (2013.01); *A61B 2017/22098* (2013.01); *A61F 2002/016* (2013.01)

(58) Field of Classification Search
CPC ...... A61F 2/013; A61F 2/01; A61F 2002/011; A61F 2002/016; A61B 17/221; A61B 17/320758; A61B 17/12172; A61B 17/12109; A61B 17/320725;
(Continued)

(56) References Cited

U.S. PATENT DOCUMENTS 6,361,545 B1 * 3/2002 Macoviak ........ A61B 17/12136
606/200
2010/0312268 A1 * 12/2010 Belson ...................... A61F 2/01
606/200

(Continued)

FOREIGN PATENT DOCUMENTS

WO      2004/043293      5/2004
WO   WO 2010014515 A2 *  2/2010  ....... A61B 17/22012

OTHER PUBLICATIONS

PCT Written Opinion and Search PCT/US2013/035346, dated Oct. 26, 2013.

*Primary Examiner* — Richard Louis
(74) *Attorney, Agent, or Firm* — Dekel Patent Ltd.; David Klein (57) ABSTRACT

A device includes a protection sleeve (10) and a retractable sheath (14) operatively connected to the protection sleeve (10), and a catheter (16) that passes through a main lumen (26) of the sleeve (10). The catheter (16) includes a heart valve treatment device arranged to pass into a lumen of the catheter (16).

13 Claims, 5 Drawing Sheets

(58) Field of Classification Search
CPC ...... A61B 17/3207; A61B 2017/22304; A61B 2017/22098; A61B 2017/00783
See application file for complete search history.

(56) References Cited

U.S. PATENT DOCUMENTS

2011/0130657 A1    6/2011  Chomas
2011/0264200 A1*  10/2011  Tran ...................... A61F 2/2436
                                                          623/2.11

* cited by examiner

PERCUTANEOUS EMBOLI PROTECTION SLEEVE

CROSS REFERENCE TO OTHER APPLICATIONS

This application is a US national phase application of PCT patent application PCT/US2013/035346, filed Apr. 5, 2013, which claims priority from U.S. Provisional Patent Application 61/621,005, filed Apr. 6, 2012, and U.S. Provisional Patent Application 61/639,929, filed Apr. 29, 2012.

FIELD OF THE INVENTION

The present invention generally relates to capturing embolic or other materials, such as during cardiovascular surgery, and particularly to a percutaneous protection sleeve, which can either serve as a guidance sleeve or slide over a catheter.

BACKGROUND OF THE INVENTION

In valve repair or replacement surgery, manipulation of calcified valves may result in dislodgment of calcified material, particles of tissue and other debris, all referred to herein as embolic debris or simply emboli. The embolic debris can migrate through the circulatory system and cause vessel occlusion, blood clots and cerebrovascular accidents, or strokes. A need therefore exists for safely containing embolic debris during cardiovascular surgery.

One method used in the past for removing embolic debris temporarily obstructs the artery and then draws the embolic debris from the vasculature by suction. A disadvantage is the temporary obstruction can threaten life or organ survival. Another method breaks up the embolic debris into small pieces for removal from the vasculature. Disadvantages include difficulty in controlling size of the fragments and possibility of damaging nearby tissue. Other methods include embolic capture or diversion by means of stand-alone filter devices, which are positioned to protect specific vessels, but that do not function as conduits or guides for delivering therapeutic devices.

SUMMARY OF THE INVENTION

The present invention seeks to provide novel devices and methods for improving the safety and efficacy of percutaneous treatment of vasculature and devices introduced into the vasculature, such as aortic valves, as is described more in detail hereinbelow. In one embodiment, there is a guidance and protection sleeve that can be positioned in the aorta or other body lumen. The guidance and protection sleeve can be used to accurately position a catheter (or new valve) for deployment by guiding the catheter (or the new valve) into the center of the native valve, without scraping the potentially calcified or atheromateous aortic wall. In another embodiment, the invention describes a percutaneous sleeve that slides over a catheter.

The term "catheter" as used herein, encompasses any percutaneous device, such as but not limited to, a catheter, cannula, guidewire, stent, certain transcatheter aortic valve implantation (TAVI) devices, and others. The catheter may be a treatment catheter, diagnostic catheter, imaging catheter, etc.

In some embodiments, the protection sleeve can create an enclosed (or partly enclosed) region above the native valve leaflets (above or below the coronary ostia), in order to capture or divert away from the cerebral vasculature any embolic debris that might be created during impact, decalcification, dilation (such as by balloon valvuloplasty) or implantation of the new valve.

In some embodiments, the device can be used for assisting the delivery of catheters through blood vessels by reducing the risk of scraping or perforating the blood vessel walls during catheter delivery and retrieval. The device can transform its shape after it is delivered, and before use in catheter delivery. For example, the device expands after delivery to the site before catheter delivery. Catheters may be delivered through a lumen in the device. The device can assist relative positioning of the catheter vis-à-vis the anatomy. The device can assist in centering the catheter in the aorta. The device can aid in the capture or diversion of embolic debris created during treatment.

There is provided in accordance with one embodiment of the present invention, a method including introducing a protection sleeve in a body lumen, wherein proximal and distal end caps are attached to proximal and distal ends, respectively, of the protection sleeve, and wherein the proximal end cap is slidingly mounted along an outer perimeter of a catheter, and the distal end cap is affixed (or alternatively can slide with respect) to a distal portion of the catheter, and one or more manipulation elements are attached to the protection sleeve, wherein the protection sleeve is in a contracted state upon entry into the body lumen, manipulating the one or more manipulation elements to slide the proximal end cap distally (or the distal end proximally, or any combination thereof) so as to radially expand the protection sleeve, and positioning a section of the protection sleeve so that it blocks emboli from passing therethrough.

In accordance with an embodiment of the present invention, the method includes allowing emboli to flow into a distal axial end portion of the protection sleeve, and to flow out of a proximal axial end portion of the protection sleeve.

In accordance with an embodiment of the present invention, the method includes manipulating the one or more manipulation elements to slide the proximal end cap proximally so as to radially contract the protection sleeve, and removing the protection sleeve from the body lumen.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
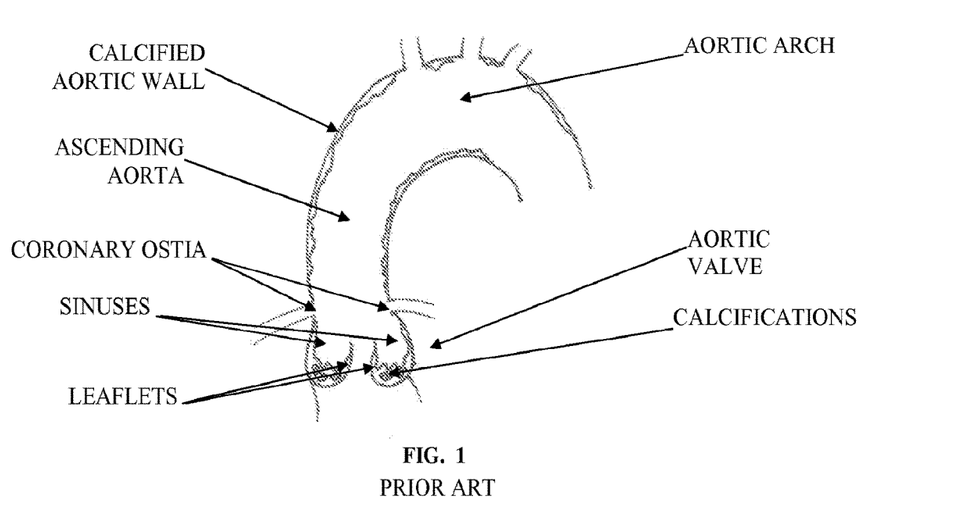
FIG. 1 is a simplified illustration of anatomy of a calcified aorta.

Reference is now made to FIG. 1, which illustrates the anatomy of a calcified aorta. The aortic valve includes three leaflets (or two leaflets in bicuspid valves) that throughout the years can develop calcifications, which reduce leaflet mobility and lead to aortic stenosis. Above the valve leaflets are the sinuses with coronary ostia, and the ascending aorta. The carotid artery takeoffs are on the upper part of the aortic arch.

Figure 2:
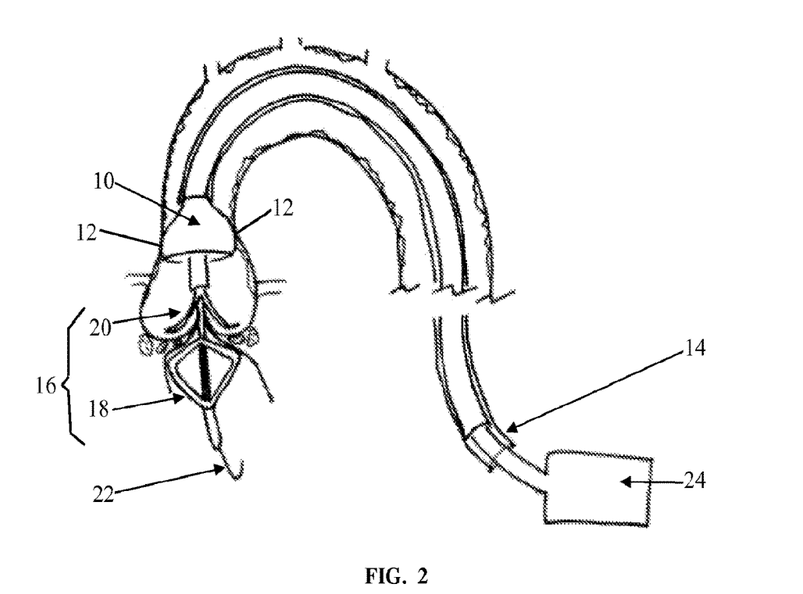
FIG. 2 is a simplified illustration of a guiding and protection sleeve, constructed and operative in accordance with a non-limiting embodiment of the present invention.

Reference is now made to FIG. 2, which illustrates a guiding and protection sleeve 10, constructed and operative in accordance with a non-limiting embodiment of the present invention. Sleeve 10 is shown in a deployed position, preferably anchored by means of one or more anchoring members 12 on its distal side to the aortic wall in the ascending aorta. A retractable sheath 14, shown in an already retracted position, may be used to open/expand the anchoring members 12.

Sleeve 10 is shown in use with a catheter 16. Without limitation, the illustrated catheter 16 is a mechanical impactor catheter, described in PCT patent applications PCT/US2009051784 or PCT/US1058810. Catheter 16 includes an impactor element 18 (in the left ventricular outflow tract (LVOT) below the valve) and a stabilizer element 20 (in the aorta above the valve). Catheter 16 crosses the valve over a guidewire 22 in a closed configuration, and is then opened for treatment. A handle 24 is used to control the operation of catheter 16.

Figure 3:
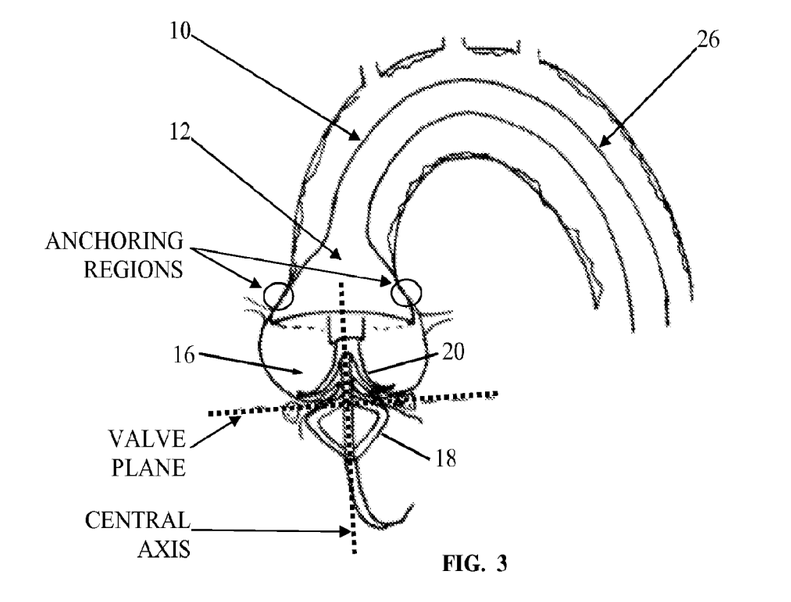
FIG. 3 is a simplified illustration of one possible function of the guidance and protection sleeve, which is to guide and control the position of a catheter relative to anatomy, such as the aorta and valve.

Reference is now made to FIG. 3, which illustrates one possible function of the guidance and protection sleeve 10, which is to guide and control the position of the catheter 16 relative to anatomy, such as the aorta and valve. Since the catheter 16 preferably goes through the main lumen of sleeve 10, the axial and transverse position of the distal part of sleeve 10 affects the transverse position of catheter 16. The position of the distal part of sleeve 16 relative to the anatomy (such as the aorta, sinuses or the aortic valve) can be established by using one or more distal anchoring members 12 (e.g., funnel, struts, wings, pads, and the like, which may be optionally expandable by balloon expansion or shape memory expansion or expanded by guidewire manipulation) that come into contact with the anatomy, or by pre-setting the shape of the guiding and protection sleeve 10 to fit the particular anatomy. This positioning function can be important in cases where the catheter 16 needs to be positioned approximately at the center of the aorta above the valve. In the case of the impactor catheter 16, the impactor element 18 can be used to center the distal portion of the impactor catheter 16 at the LVOT, and the distal anchoring member(s) 12 of the guidance and protection sleeve can be used to ensure that the stabilizer element 20 is aligned axially. This means the central axis of catheter 16 passing through the stabilizer 20 and impactor 18, approximately coincides with the central axis of the ascending aorta, and is approximately perpendicular to the valve plane.

Figure 4:
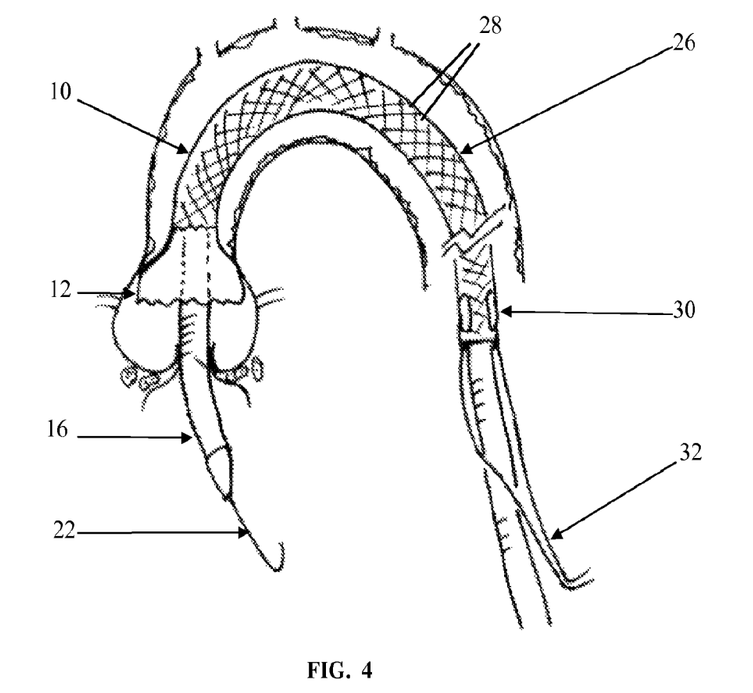
FIG. 4 is a simplified illustration of another non-limiting embodiment of the guiding and protection sleeve, and another function that it potentially has, to reduce the potential scraping of the vascular walls by the catheter during delivery and retrieval of the catheter.

Reference is now made to FIG. 4, which illustrates another non-limiting embodiment of the guiding and protection sleeve 10, and another function that it potentially has, namely to reduce the potential scraping, dissection or perforation of the vascular walls by the catheter 16 during delivery and retrieval of the catheter 16. In this embodiment, sleeve 10 includes distal anchoring member(s) 12 and a main lumen 26. The main lumen 26 is preferably designed to allow perfusion of blood through pores 28 in its material. There are numerous methods known in the art to produce such perfusion, such as, but not limited to, braiding of metal wires, a laser-cut metal tube, a metal structure (braided or other) covered by a polymer with pores, GORE-TEX material, etc. If the pores 28 surrounding the main lumen are small enough (preferably in the range of 100-500 microns), then blood can perfuse through these pores, but any relevant (potentially damaging) embolic debris remains within the main lumen and flow downstream.

The embodiment described in FIG. 4 further includes larger, embolic release pores 30, which are preferably more than 500 microns in size. Large pores 30 can be placed in the descending aorta, so that any potential emboli flowing through the main lumen can be released to the descending aorta, avoiding the cerebral vasculature, thereby reducing the risk for stroke. It is also possible not to include embolic release pores 30. In such case, any potential emboli will be trapped inside the main lumen, and then removed from the patient body when sleeve 10 is finally removed. Optionally, sleeve 10 may include main lumen 26 without any pores at all, e.g., a solid polymer with or without a metallic structure. If main lumen 26 does not have pores, then blood cannot perfuse through main lumen 26, and some pores (large or small) preferably need to be incorporated downstream, in order to allow proper blood flow through the main lumen. It will readily be understood that any combination of cover types, porous or non-porous, may be used in any of the segments of sleeve 10, such as in the distal anchoring member(s) 12, over segments of the main lumen 26, and downstream in the descending aorta. The distal anchoring member(s) 12 can be designed to cover the entire cross-section of the aorta or part of the cross section of the aorta. It is also possible not to include distal anchoring of sleeve 10, but to hold or fix sleeve 10 on its proximal side, in the vicinity of the introducer shaft, and to use the mechanical strength of the sleeve structure in order to hold its distal part in place so it does not migrate.

FIG. 4 further shows retraction elements 32 (e.g., wires), that can be used to hold sleeve 10 in place during the procedure, and then to retrieve sleeve 10 at the end of the procedure. FIG. 4 further shows the catheter 16 (such as the impactor catheter, TAVI delivery system, balloon valvuloplasty catheter, decalcification catheter, etc.) as delivered through sleeve 10. It can be readily understood that the guiding and protection sleeve 10 acts as a buffer or protection layer separating the catheter 16 from the vessel wall, and especially from the aortic arch and ascending aorta, where scraping of the wall can lead to release of debris, and even perforation.

Figure 5:
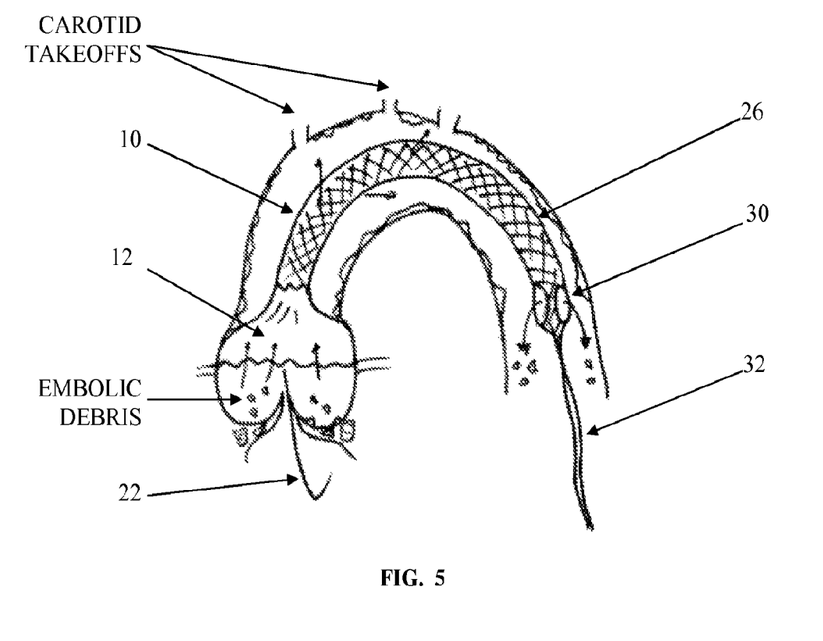
FIG. 5 is a simplified illustration of a function of the guiding and protection sleeve as a diverter of potential calcific emboli.

Reference is now made to FIG. 5, which illustrates the function of the guiding and protection sleeve 10 as a diverter of potential calcific emboli, if such embolic debris are created following treatment of the aortic valve. Emboli are collected by the distal anchoring member(s) 12, flow through the main lumen 26 and out of the emboli release pores 30, avoiding the carotid takeoffs. If either the distal anchoring member(s) 12 or the main lumen 26 of sleeve 10 are made of porous material, then blood can flow through the pores into the aorta and carotid takeoffs.

Figure 6:
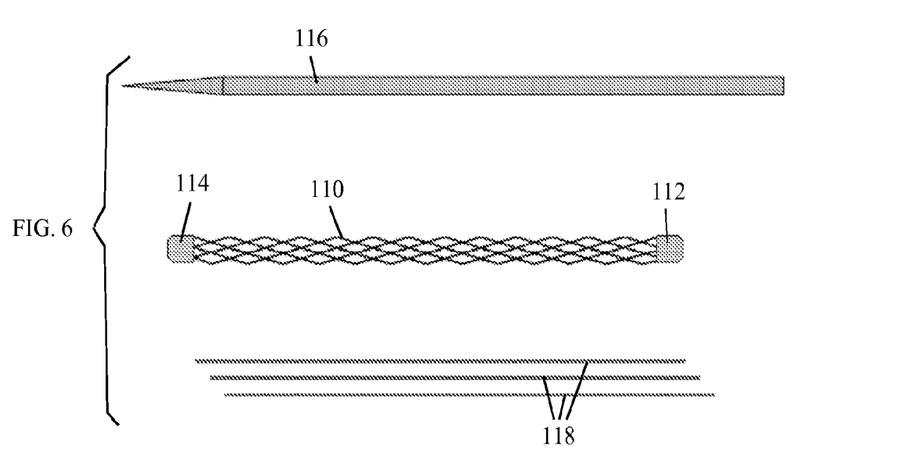
FIGS. 6 and 7 are simplified illustrations of a protection sleeve, constructed and operative in accordance with a non-limiting embodiment of the present invention, respectively before and after assembly on a catheter, wherein in FIG. 7, the protection sleeve is in a contracted state prior to delivery into a body lumen.
Figure 7:
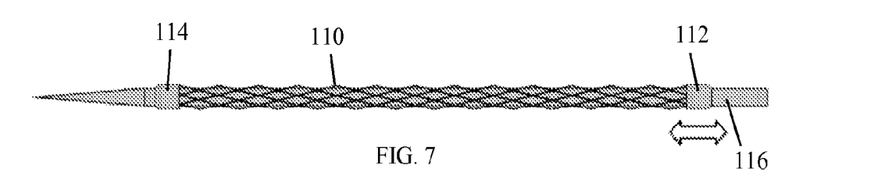

Reference is now made to FIGS. 6 and 7, which illustrate a protection sleeve 110, constructed and operative in accordance with a non-limiting embodiment of the present invention. Protection sleeve 110 may be constructed from a medically safe plastic, metal or other material, such as without limitation, stainless steel, shape memory alloy, titanium alloy, polymers, etc.

In one preferred construction, protection sleeve 110 is formed of braided wire or mesh. Constructing protection sleeve 110 with braided wire technology has the advantage that the "pitch" of each wire can be relatively large when in the contracted state and then relatively small when in the fully expanded state. In the contracted state, the pores created by the braided wires have elongated "diamond" shapes (long and narrow) and therefore add minimal thickness to the catheter. In the expanded state, the pores have transverse "diamond" shapes (short and wide), that is, a very small pore size, which is advantageous for embolic protection. In summary, using braided wire technology, a relatively low profile (but long) sleeve can transform into a large expanded diameter sleeve with very small pore size.

End caps 112 and 114 are attached to proximal and distal ends, respectively, of protection sleeve 110. End caps 112 and 114 may be made of the same or different material as protection sleeve 110. Protection sleeve 110 together with end caps 112 and 114 are assembled on a catheter 116. The proximal end cap 112 is arranged to slide along the outer perimeter of catheter 116, whereas the distal end cap 114 is affixed to a distal portion of catheter 116. Alternatively, the proximal cap can be fixed, and the distal cap can slide, or both caps can slide, as long as the length of the sleeve can be varied.

One or more manipulation elements 118, such as but not limited to, push and/or pull wires, or alternatively shafts, are attached to protection sleeve 110. As will be explained below, manipulation elements 118 may be used to radially expand or contract protection sleeve 110 for deployment of removal of the sleeve.

In FIG. 7, protection sleeve 110 is in a contracted state prior to delivery into a body lumen. "Contracted" refers to the radial direction about the catheter 116; the protection sleeve 110 is elongate in the axial direction in this state. When in the axially elongated state, protection sleeve 110 adds minimal thickness to the contour of catheter 116.

Figure 8:
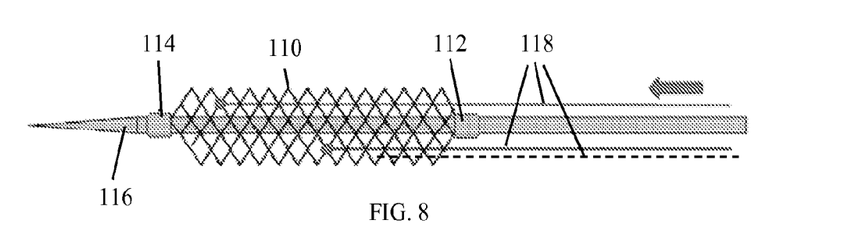
FIG. 8 is a simplified illustration of the protection sleeve in a semi-expanded state during delivery into a body lumen, in accordance with a non-limiting embodiment of the present invention.

Reference is now made to FIG. 8, which illustrates protection sleeve 110 in a semi-expanded state during delivery into the body lumen. The manipulation elements 118 are manipulated to push sleeve 110 towards the distal end of catheter 116. It is noted that the axial length of protection sleeve 110 decreases during radial expansion of the sleeve. In one embodiment of the invention, the manipulation elements 118 cause uniform expansion and contraction of sleeve 110. In another embodiment of the invention, a plurality of manipulation elements 118 can be affixed to different axial or radial positions of sleeve 110, so that some of manipulation elements 118 can be manipulated independently and/or differently than other manipulation elements 118 (as shown in broken lines in FIG. 8). For example, some can push while others remain unused; some can be pushed to different degrees than others. This can be used to effect non-uniform expansion and contraction of sleeve 110 (e.g., creating different sinusoidal or wavy patterns).

Figure 9:
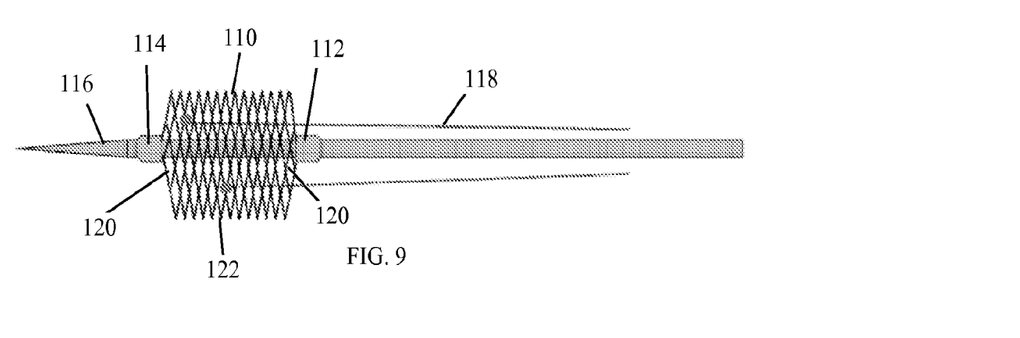
FIG. 9 is a simplified illustration of the protection sleeve in a fully-expanded, deployed state after delivery into a body lumen, in accordance with a non-limiting embodiment of the present invention.

Reference is now made to FIG. 9, which illustrates protection sleeve 110 in a fully-expanded, deployed state after delivery into the body lumen. In this configuration, protection sleeve 110 reaches its maximum expanded diameter and shortest axial length. The braided or meshed construction of sleeve 110 allows for different size pores at different positions in the sleeve. For example, at axial end portions 120 of sleeve 110, there is a relatively open mesh (i.e., large pore size). This facilitates entry and exit of emboli into the sleeve 110. In contrast, at a middle section 122 of sleeve 110, extending between the end portions 120, the mesh or braid is very dense (i.e., small pore size). This ensures that virtually no emboli will pass through middle section 122 of sleeve 110.

Figure 10:
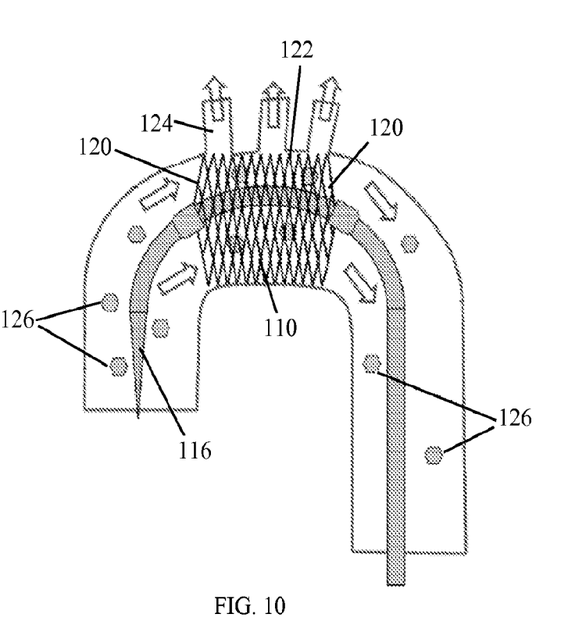
FIG. 10 is a simplified illustration of the deployed protection sleeve positioned to protect carotid takeoffs from emboli entering therein, in accordance with a non-limiting embodiment of the present invention.

Reference is now made to FIG. 10, which illustrates the deployed protection sleeve 110 deployed in the aortic arch and positioned to protect carotid takeoffs 124 from emboli entering therein, in accordance with a non-limiting embodiment of the present invention. The protection sleeve 110 diverts and traps potential calcific emboli, if such embolic debris are created during a surgical procedure, such as but not limited to, valve repair or replacement surgery. Emboli 126 flow into the distal axial end portion 120 of sleeve 110 and flow out of the proximal axial end portion 120 of sleeve 110. The middle section 122 of sleeve 110 blocks emboli 126 from entering the carotid takeoffs 124. Protection sleeve 110 does not impede or interfere with blood flow. After the procedure is completed, the sleeve 110 can be retracted to its contracted state and removed from the lumen. In another possible embodiment, the typical pore size of section 120 "downstream" is designed small enough in order to capture emboli that are large enough. Section 120 located "upstream" can have an increased pore size, so that emboli can flow into the protection sleeve through the "eyes" and then be captured downstream.

What is claimed is:

1. A device comprising:
a protection sleeve; and
a retractable sheath operatively connected to said protection sleeve; and
a catheter that passes through a main lumen of said sleeve, wherein said catheter comprises a heart valve treatment device arranged to pass into a lumen of said catheter; and
wherein said heart valve treatment device comprises a stabilizer element, and wherein said protection sleeve comprises one or more distal anchoring members operative to align said stabilizer element axially so that a central axis of said catheter, which passes through said stabilizer element, coincides with a central axis of a lumen of a patient.

2. The device according to claim 1, wherein at least one anchoring member is located in a portion of said protection sleeve.

3. The device according to claim 2, wherein said retractable sheath, upon retraction thereof, is operative to expand said at least one anchoring member.

4. The device according to claim 1, wherein said heart valve treatment device further comprises a calcification treatment element.

5. The device according to claim 1, wherein said main lumen comprises pores through which blood can perfuse embolic debris cannot.

6. The device according to claim 1, wherein said main lumen comprises embolic release pores through which embolic debris can pass.

7. A device comprising:
a protection sleeve;
proximal and distal end caps attached to proximal and distal ends, respectively, of said protection sleeve;
a catheter, wherein said proximal end cap and said distal end cap are movable one with respect to the other along an outer perimeter of said catheter; and
one or more manipulation elements which are attached to said protection sleeve, wherein manipulation of said one or more manipulation elements is operative to radially expand or contract said protection sleeve;
and wherein said catheter comprises a heart valve treatment device arranged to pass into a lumen of said catheter, said heart valve treatment device comprising a stabilizer element, and wherein said protection sleeve comprises one or more distal anchoring members operative to align said stabilizer element axially so that a central axis of said catheter, which passes through said stabilizer element, coincides with a central axis of a lumen of a patient.

8. The device according to claim 7, wherein said protection sleeve is made of wire braid.

9. The device according to claim 7, wherein said one or more manipulation elements comprise push and/or pull wires or shafts.

10. The device according to claim 7, wherein said one or more manipulation elements are operative to cause uniform expansion and contraction of said protection sleeve.

11. The device according to claim 7, wherein a plurality of said manipulation elements are affixed at different positions of said protection sleeve, so that at least one of said manipulation elements is manipulable independently of another of said manipulation elements.

12. The device according to claim 7, wherein pores of axial end portions of said protection sleeve have a size than pores of a middle section of said protection sleeve, extending between said end portions.

13. The device according to claim 7, wherein said protection sleeve is made of a material with pores said protection sleeve has an expandable portion transformable to an expanded state radially outwards, and said protection sleeve in a contracted state is axially longer than said expandable portion in the expanded state, and the pores of said expandable portion in the expanded state are smaller in size than the pores of the protection sleeve in the contracted state.

* * * * *